(12) United States Patent
Thorwarth

(10) Patent No.: US 10,556,033 B2
(45) Date of Patent: Feb. 11, 2020

(54) SURFACE COATING FOR A MEDICAL INSTRUMENT, MEDICAL INSTRUMENT HAVING A SURFACE COATING, AND METHOD FOR PRODUCING A SURFACE COATING FOR A MEDICAL INSTRUMENT

(71) Applicant: IMT Masken und Teilungen AG, Greifensee (CH)

(72) Inventor: Goetz Thorwarth, Lindau (CH)

(73) Assignee: IMT MASKEN UND TEILUNGEN AG, Greifensee (CH)

( * ) Notice: Subject to any disclaimer, the term of this patent is extended or adjusted under 35 U.S.C. 154(b) by 0 days.

(21) Appl. No.: 16/001,964

(22) Filed: Jun. 7, 2018

(65) Prior Publication Data
US 2018/0353635 A1 Dec. 13, 2018

(30) Foreign Application Priority Data
Jun. 13, 2017 (DE) .................. 10 2017 112 941

(51) Int. Cl.
B32B 3/00 (2006.01)
A61L 2/28 (2006.01)
(Continued)

(52) U.S. Cl.
CPC .............. *A61L 2/28* (2013.01); *A61L 2/07* (2013.01); *A61L 27/306* (2013.01); *A61L 31/088* (2013.01); *A61B 17/3211* (2013.01); *A61F 2/4455* (2013.01); *A61F 2250/0097* (2013.01); *A61F 2310/0055* (2013.01);
(Continued)

(58) Field of Classification Search
CPC ... A61L 2/07; A61L 2/28; A61L 27/30; A61L 31/082
See application file for complete search history.

(56) References Cited

U.S. PATENT DOCUMENTS

2003/0211618 A1\* 11/2003 Patel .................. A61L 2/07 436/38
2012/0040102 A1\* 2/2012 Meredith .............. A61L 27/30 427/458
(Continued)

FOREIGN PATENT DOCUMENTS

EP 0560534 A1 9/1993
EP 0774618 A1 5/1997
(Continued)

OTHER PUBLICATIONS

Database WPI, Week 201577, Thomas Scientific, London, GB, AN 2015-69977U, XP002786001, Dec. 2017.

*Primary Examiner* — Elizabeth E Mulvaney
(74) *Attorney, Agent, or Firm* — Leydig, Voit & Mayer, Ltd.

(57) ABSTRACT

A surface coating for a medical instrument includes an interference filter having at least one dielectric layer and at least one metallic layer arranged one above another. At least one of the at least one metallic layer and the at least one dielectric layer is adapted to be structurally altered by action of a corrosive environment on the surface coating such that the surface coating is convertible from a first state to a second state. In the first state, the surface coating has a first spectral reflectivity. In the second state, the surface coating has a second spectral reflectivity that is different from the first spectral reflectivity.

13 Claims, 5 Drawing Sheets

(51) Int. Cl.
*A61L 2/07* (2006.01)
*A61L 27/30* (2006.01)
*A61L 31/08* (2006.01)
*A61B 17/3211* (2006.01)
*A61F 2/44* (2006.01)

(52) U.S. Cl.
CPC .............. *A61F 2310/00401* (2013.01); *A61F 2310/00407* (2013.01); *A61F 2310/00425* (2013.01); *A61F 2310/00431* (2013.01); *A61F 2310/00485* (2013.01); *A61F 2310/00491* (2013.01); *A61F 2310/00497* (2013.01); *A61F 2310/00544* (2013.01); *A61L 2202/21* (2013.01); *A61L 2202/24* (2013.01); *A61L 2420/02* (2013.01); *A61L 2420/08* (2013.01)

(56) References Cited

U.S. PATENT DOCUMENTS

| 2016/0122865 | A1* | 5/2016 | Sequeda Osorio | A61L 27/30 428/216 |
| 2017/0007346 | A1 | 1/2017 | Kikuchi | |
| 2017/0197015 | A1* | 7/2017 | Desai | A61L 31/022 |
| 2017/0261381 | A1* | 9/2017 | Patel | G01K 3/04 |

FOREIGN PATENT DOCUMENTS

| JP | 2015198819 A | 11/2015 |
| JP | 2015198910 A | 11/2015 |
| WO | WO 2006098813 A1 | 9/2006 |

* cited by examiner

SURFACE COATING FOR A MEDICAL INSTRUMENT, MEDICAL INSTRUMENT HAVING A SURFACE COATING, AND METHOD FOR PRODUCING A SURFACE COATING FOR A MEDICAL INSTRUMENT

CROSS-REFERENCE TO PRIOR APPLICATION

Priority is claimed to German Patent Application No. DE 10 2017 112 941.3, filed on Jun. 13, 2017, the entire disclosure of which is hereby incorporated by reference herein.

FIELD

The present invention relates to a surface coating for a medical instrument, a medical instrument having a surface coating, and to a method for producing a surface coating for a medical instrument.

The present invention further relates to a surface coating for a medical device intended for use under sterile conditions, for example, for therapeutic applications on the human or animal body. In the following, the term "medical instrument" will be understood to refer not only to surgical hand instruments, such as scalpels, but to any type of device that is intended for medical purposes and accordingly has to be kept sterile. In particular, devices intended for implantation into the human or animal body will also be understood to fall under the term "medical instrument." Furthermore, term "medical instrument" will also be used to refer to "microfluidic devices (e.g., so-called "flow cells"), such as are used, for example, for diagnostic purposes, and in particular for DNA sequencing.

BACKGROUND

In medical applications, single-use products are widespread. These are medical instruments which are not intended for multiple use for various reasons (e.g., insufficient sterilizability, material changes caused by clinical reprocessing, or because of the mechanical durability rating). Reuse on a patient (e.g., for reasons of economy) may present a health risk to the patient.

This results in the need to provide medical instruments intended for single use with a marking that indicates impermissible multiple use.

JP 2015 198 819 A describes a medical instrument having a warning indicator that is based on an imprint made with a color-changing ink. When the medical instrument is subjected to a sterilization treatment in order to be reused, the ink changes its color from violet to blue, so that a warning becomes readable.

SUMMARY

In an embodiment, the present invention provides a surface coating for a medical instrument. The surface coating includes an interference filter having at least one dielectric layer and at least one metallic layer arranged one above another. At least one of the at least one metallic layer and the at least one dielectric layer is adapted to be structurally altered by action of a corrosive environment on the surface coating such that the surface coating is convertible from a first state to a second state. In the first state, the surface coating has a first spectral reflectivity. In the second state, the surface coating has a second spectral reflectivity that is different from the first spectral reflectivity.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1A:
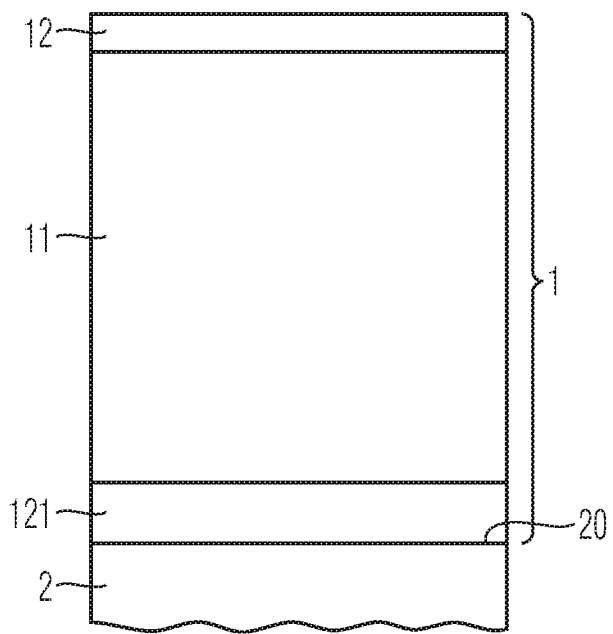
FIG. 1A is a vertical cross-sectional view showing a portion of a surface coating in a first state.

The inventor has recognized that the known approach from JP 2015 198 819 A has the disadvantage that the warning indicator is attached separately to the medical instrument and, accordingly, changes and possibly negatively affects the dimensions of the instrument and/or its mechanical properties at the respective position. Thus, it is required to provide space for the marking on the instrument. This space is then no longer available for the functional design of the instrument. It is also conceivable that such ink-based warning indicator may be unintentionally or deliberately removed from the medical instrument.

An embodiment of the present invention provides a marking that permits detection of an accidental reuse of a medical instrument and performs its indicating function reliably and irreversibly, without changing or only insignificantly changing the dimensions or mechanical properties of the instrument. In addition, the marking should be biocompatible in accordance with the standard requirements in medical applications.

According to an embodiment for providing a surface coating for a medical instrument, the surface coating including an interference filter having at least one dielectric layer and at least one metallic layer arranged one above another. In a first state, the surface coating has a first spectral reflectivity. The at least one metallic layer and/or the at least one dielectric layer are/is adapted to be structurally altered by the action of a corrosive environment on the surface coating, whereby the surface coating can be converted to a second state. In the second state, the surface coating has a second spectral reflectivity that is different from the first spectral reflectivity.

An embodiment of the present invention is based on the concept that one or more metallic layers and/or one or more dielectric layers in a metal-dielectric interference filter composed of a plurality of solid layers can be altered by corrosive influences in such a way that an irreversible change in color occurs. To this end, one or more transparent dielectric layers (e.g., of titanium dioxide) and one or more metallic layers (e.g., titanium as well as corrosion-resistant tantalum) are combined in a multi-layer coating so as to produce an interference filter having a first spectral reflectivity. During clinical reprocessing of the medical instrument or during its normal initial use (e.g., in the case of a microfluidic device), the surface coating is exposed to a corrosive environment. Because of this, one or more metallic layers are/is oxidized and thus made transparent and/or one or more metallic or dielectric layers are/is delaminated or dissolved. As a result, due to the altered structure of the interference filter or the altered optical properties of the at least one layer, the interference filter has a second spectral reflectivity; i.e., the surface coating now gives a different color appearance than before.

The term "corrosive environment" will be used herein based on the definition commonly used chemistry, according to which corrosion is a chemical or electrochemical reaction of a material with substances in its environment, which results in a measurable alteration of the material. Accordingly, a corrosive environment is an environment that facilitates or promotes corrosion. The action of a corrosive environment may be brought about, for example, by bringing the surface coating into contact with a corrosive medium.

Thus, metals and alloys which may be used for the metallic layers of the device according to the present invention include, for example, those which are corrosively degraded, for example, under typical conditions of clinical reprocessing—such as magnesium (Mg), iron (Fe) or calcium (Ca)—or which form a transparent oxide, such as aluminum (Al), titanium (Ti), zirconium (Zr), niobium (Nb), molybdenum (Mo), tantalum (Ta) or tungsten (W). In a refinement, a combination of a low-resistance metal and a high-resistance metal may be provided. Examples of combinations that may be used in medical applications include titanium/tantalum, titanium/tungsten and aluminum/niobium because in those combinations, the metallic elements in the layered structure are capable of surviving a clinical reprocessing procedure without being oxidized.

The different layers of the interference filter can be produced with the required accuracy on commercially available equipment using coating techniques per se known in the art. Depending on the specific application, different variants of physical or chemical vapor deposition may for example be used, such as reactive magnetron sputtering, reactive arc evaporation, electron beam evaporation or plasma-enhanced chemical vapor deposition.

A marking applied directly to a medical instrument using such coating methods may be designed such that it meets the biocompatibility requirements in medical applications without significantly changing the dimensions of the medical instrument in an undesired way.

For example, in a specific embodiment, a total vertical thickness of the surface coating may be, for example, less than 1000 nm, such as less than 600 nm, or even less than 500 nm.

In a specific embodiment, the at least one metallic layer is composed of titanium. Such a layer can be oxidized to titanium dioxide and made transparent, for example by a sterilization treatment, such as a treatment with a base.

Also, the at least one metallic layer may be composed of magnesium. A magnesium layer can oxidize under the action of the corrosive environment, for example during a sterilization treatment by autoclaving, and, as a result, may delaminate.

The at least one dielectric layer may be composed of, for example, titanium dioxide. Titanium dioxide is optically transparent and therefore suitable as a layer component in a metal-dielectric interference filter.

In a specific embodiment, when illuminated with white light, the surface coating has a first color in the first state and a second color in the second state, the second color being different from the first color. For example, the first color may be in the green-blue region of the spectrum, and the second color may be in the orange-red region of the spectrum (or vice versa).

Furthermore, the first spectral reflectivity may have a first reflectivity maximum at a first wavelength, and the second spectral reflectivity may have a second reflectivity maximum at a second wavelength, a difference between the second wavelength and the first wavelength being at least 100 nm, such as at least 150 nm, or even at least 200 nm. In this way, it can be ensured that exposure of the surface coating to the corrosive environment results in a color change that is clearly perceptible to the human eye. For example, the first wavelength may be in the red region of the spectrum, and the second wavelength may be in the green-blue region of the spectrum.

In an embodiment, the at least one metallic layer is adapted to be oxidized by the action of the corrosive environment, whereby the surface coating can be converted to the second state. For example, the metallic layer may be adapted to become dielectric and transparent by oxidation, whereby the optical properties of the interference filter change.

Alternatively or additionally, the at least one metallic layer may be adapted to detach from another layer of the surface coating under the action of the corrosive environment, whereby the surface coating can be converted to the second state. For example, the metallic layer may delaminate under the action of the corrosive environment (e.g., during a sterilization treatment) and be completely removed, possibly together with other layers located thereabove.

It is also within the scope of an embodiment of the present invention that the at least one dielectric layer may be adapted to detach from another layer of the surface coating under the action of the corrosive environment, whereby the surface coating can be converted to the second state. It is possible, for instance, that a dielectric layer of a water-soluble transparent salt, such as sodium chloride (NaCl), may dissolve under the action of the corrosive environment, so that other layers possibly located thereabove are also delaminated.

In a specific embodiment, the surface coating may be converted to the second state by a sterilization treatment in which the surface coating is exposed to the corrosive environment.

In an embodiment, the sterilization treatment includes an autoclaving process. For example, the sterilization treatment is an autoclaving process. During the autoclaving process, for example, the surface coating may be exposed to temperatures in the range of from 121° C. to 135° C. at an absolute pressure of from 1 to 5 bar for a period of from 1 to 30 minutes. Such conditions can provide the corrosive environment for converting the surface coating to the second state.

Alternatively or additionally, the sterilization treatment may include a treatment of the surface coating with a base, such as a base having a pH greater than 10. For example, the sterilization treatment may be a treatment of the surface coating with a base, such as a base having a pH greater than 10.

The at least one metallic layer may be adapted to increase its optical transparency or to change from an optically non-transparent state to an optically transparent state under the action of the corrosive environment. This may be accomplished, for example, through oxidation, whereby the metallic layer may also become a transparent dielectric layer.

In a refinement, the interference filter includes a plurality of dielectric layers and/or a plurality of metallic layers. By suitably designing such a stack of a plurality of metallic and/or dielectric layers, it possible to obtain the desired color characteristics for the surface coating in the first and second states, respectively. For example, first, the materials suitable for the respective medical instrument may be selected (according to the mechanical and biocompatibility requirements). Then, a first stack of a plurality of layers made of these materials may be designed and optimized in its interference properties so as to produce a first color appearance. Moreover, a second stack may be designed and optimized for a second color appearance that is different from the first color appearance. Then, the two designs may be combined by adjusting the layer thicknesses or incorporating a delaminating intermediate layer into the stack, so that the first color appearance changes to the second color appearance under the action of the corrosive environment.

According to an embodiment of the present invention, a medical instrument is provided with a surface coating according to an embodiment of the invention. Therefore, what has been said with respect to the surface coating according to embodiments of the present invention is equally applicable to the medical instrument and vice versa.

In a specific embodiment, the medical instrument is a medical hand instrument, such as a surgical hand instrument or a part thereof, such as a scalpel or a surgical drill. Alternatively, the medical instrument may also be a device intended for implantation into the human or animal body, such as an intervertebral cage ("lumbar cage"). It is also possible that the medical instrument may be a microfluidic device, such as a so-called "flow cell." Such microfluidic devices are frequently used in the context of molecular medical techniques for diagnostic purposes, such as in DNA sequencing. During normal initial use and/or during a sterilization treatment of such a microfluidic device, the surface coating may be exposed to a corrosive environment.

According to another embodiment, a method for producing a surface coating for a medical instrument is provided. Such method includes providing a medical instrument having a surface, and producing an interference filter on the surface, the interference filter including at least one dielectric layer and at least one metallic layer arranged one above another. In a first state, the surface coating has a first spectral reflectivity, and the at least one metallic layer and/or the at least one dielectric layer are/is adapted to be structurally altered by the action of a corrosive environment on the surface coating, whereby the surface coating can be converted to a second state. In the second state, the surface coating has a second spectral reflectivity that is different from the first spectral reflectivity.

FIG. 1A shows in vertical cross section a portion of a surface coating 1 for a medical instrument 2 in accordance with a first exemplary embodiment. Medical instrument 2 may be a single-use implant for insertion into the human body, such as an intervertebral cage ("lumbar cage"). Surface coating 1 is disposed on a surface 20 of medical instrument 2. Surface 20 may be formed, for example, from a substrate layer of a thermoplastic material, such as polyether ether ketone (PEEK).

Surface coating 1 may be formed on surface 20 by electron beam evaporation, for example. This may be done in a masked process, so that surface coating 1 may be deposited in the form of, for example, a warning label of the type "DO NOT USE."

In the first state depicted in FIG. 1A, surface coating 1 includes a stack composed of a first metallic layer 121, a dielectric layer 11, and a second metallic layer 12. First metallic layer 121 is disposed on surface 20 of the substrate layer of medical instrument 2. Dielectric layer 11 is disposed on metallic layer 121. Second metallic layer 12 is disposed on dielectric layer 11 and finishes stack 1 off at the top.

First metallic layer 121 may be composed of tantalum. In the vertical direction; i.e., a direction normal to surface 20 of substrate layer 2, first metallic layer 121 may, for example, have a thickness in the range of from 10 nm to 90 nm, such as in the range of from 30 nm to 70 nm.

In a specific embodiment, dielectric layer 11 is composed of titanium dioxide ($TiO_2$). A vertical thickness of dielectric layer 11 may, for example, be in the range of from 55 nm to 65 nm, such as in the range of from 57 nm to 63 nm.

In a specific embodiment, second metallic layer 12 is composed of titanium. A vertical thickness of second metallic layer 12 may, for example, be in the range of from 7 nm to 13 nm, such as in the range of from 8 nm to 12 nm.

In a specific embodiment, first metallic layer 121 is composed of tantalum and is 50 nm thick, dielectric layer 11 is composed of titanium dioxide and is 60 nm thick, and second metallic layer 12 is composed of titanium and is 10 nm thick.

In the first state shown in FIG. 1A, surface coating 1 has a first spectral reflectivity; i.e., a characteristic wavelength dependence of the reflection of light in the optical region. Thus, in the first state, illumination of surface coating 1 with white light produces a first color appearance to the human eye. If second metallic layer 12 is, for example, a 10 nm thick titanium layer, dielectric layer 11 is a 60 nm thick titanium dioxide layer, and the first metallic layer is a 50 nm thick tantalum layer, then a blue color appearance is produced as a result of the selected interference behavior and a strong reflection at first metallic layer 121. The second metallic layer of the aforementioned thickness may already be substantially transparent, the color appearance being determined essentially by the thickness of the dielectric layer.

Figure 1B:
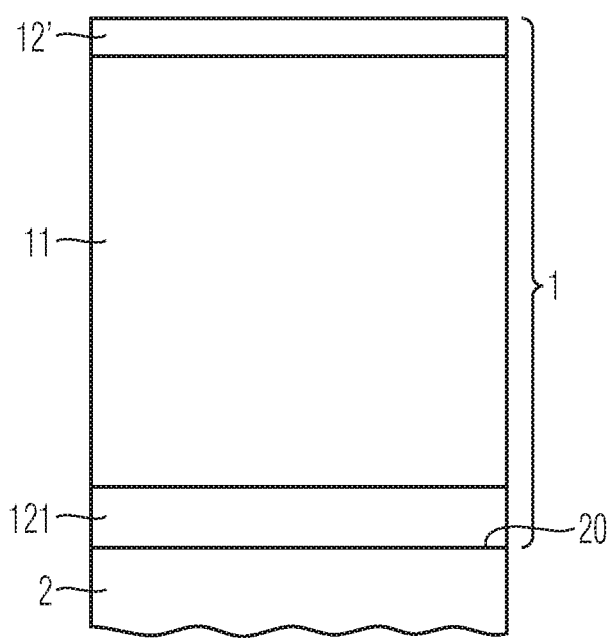
FIG. 1B shows the surface coating of FIG. 1A in a second state after a sterilization treatment.

If now, medical instrument 2 is clinically reprocessed by a sterilization treatment contrary to its purpose, surface coating 1 is thereby irreversibly converted to a second state shown in FIG. 1B. During the sterilization treatment, surface coating 1 may, for example, be exposed to a base. In clinical practice, it is common to perform reprocessing procedures at pH levels of 10 or higher. When surface coating 1 is exposed to a base with a pH>10, the covering second metal layer 12 is irreversibly structurally altered by oxidation. If second metal layer 12 is composed of titanium, then a covering layer 12' of titanium dioxide is thereby produced, whereby second metallic layer 12 is converted to a transparent dielectric layer 12'. Thus, in combination with underlying dielectric layer 11, which, in the exemplary embodiment, is also composed of titanium dioxide, a titanium dioxide layer having a thickness of, for example, approximately 70 nm is formed as a top layer of surface coating 1 in the second state. In the second state, as a result of this new layer thickness, a color appearance is produced which is different than before. Taking into account the refractive index of titanium dioxide, which is about 2.4 and lengthens the optical path by a corresponding factor, the new layer thickness is equal to, for example, a quarter wavelength of red light. Red light components which are reflected at the interface with the covering titanium dioxide layer 12' interfere constructively with red light components which enter titanium dioxide layers 12', 11 and are reflected at the inner interface with first metallic (tantalum) layer 121, because they experience a phase shift of 180° as they enter the uppermost titanium dioxide layer 12' and then travel a total distance of about half a (red) wavelength before exiting titanium dioxide layer 12' (taking into account the refractive index of titanium dioxide). Apart from this constructive interference, destructive interferences of other spectral components may also play a role for the overall color appearance produced.

As an ultimate result, the spectral reflectivity in the second state is irreversibly altered compared to the first state to the effect that red light is reflected to a greater extent. Thus, in the second state, surface coating 1 produces a red color appearance when illuminated with white light. Thus, for example, the label "DO NOT USE" appears in red letters on medical instrument 2.

Figure 2A:
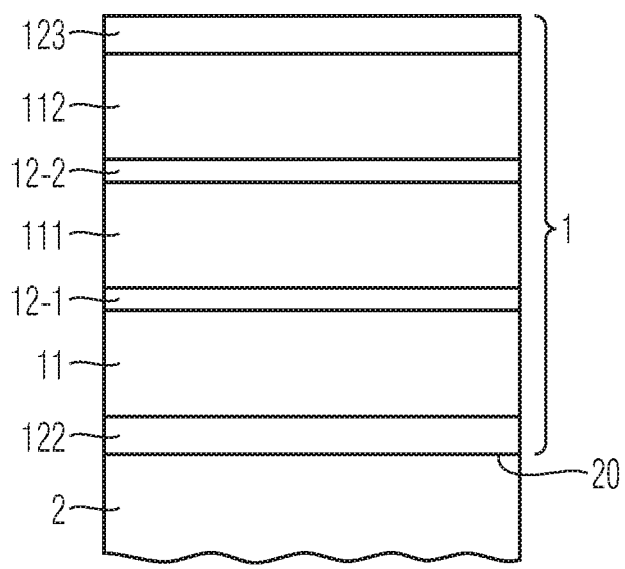
FIG. 2A is a vertical cross-sectional view showing a portion of a surface coating in a first state.
Figure 2B:
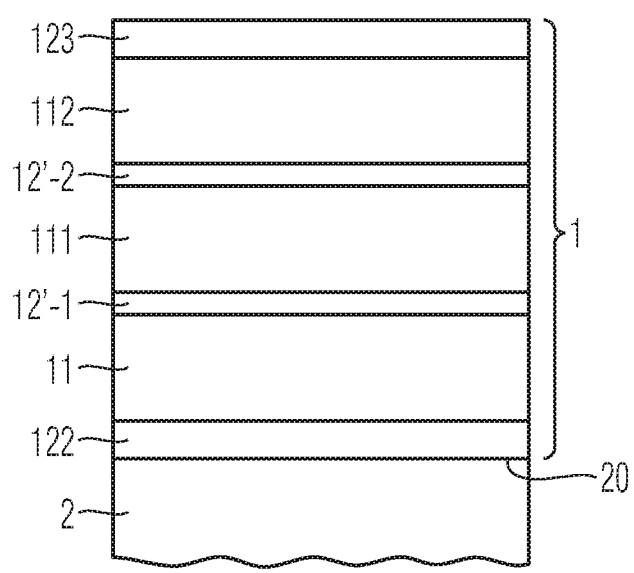
FIG. 2B shows the surface coating of FIG. 2A in a second state subsequent to a sterilization treatment.

FIGS. 2A and 2B show a second exemplary embodiment of a surface coating 1 of a medical instrument 2. FIG. 2A shows in vertical cross section a portion of a surface coating 1 in a first state.

In this specific embodiment, medical instrument 2 may be a surgical hand instrument or a part thereof, such as a single-use drill. Surface coating 1 may be formed on a surface 20 of medical instrument 2 by masked reactive magnetron sputtering, for example. For example, initially, surface 20 of medical instrument 2 (i.e., without surface coating 1) is formed from a substrate layer of stainless steel, such as the commonly used 316L steel.

In the first state shown in FIG. 2A, surface coating 1 includes a stack composed of the following layers: a first metallic layer 122 disposed on surface 20 of medical instrument 2; a first dielectric layer 11; a second metallic layer 12-1, a second dielectric layer 111; a third metallic layer 12-2; a third dielectric layer 112; and a fourth metallic layer 123. These layers are arranged one above another in the order in which they are mentioned above, starting at surface 20 of medical instrument 2, so that fourth metallic layer 123 finishes stack 1 off at the top.

First metallic layer 122 and fourth metallic layer 123 may be composed of tantalum. First metallic layer 122 and fourth metallic layer 123 may, for example, each have a thickness in the range of from 25 nm to 35 nm, such as in the range of from 28 nm to 32 nm.

First dielectric layer 11, second dielectric layer 111 and third dielectric layer 112 may be composed of titanium dioxide, for example. A vertical layer thickness of each of first dielectric layer 11, second dielectric layer 111 and third dielectric layer 112 may, for example, be in the range of from 60 nm to 70 nm, such as in the range of from 63 nm to 67 nm.

In a specific embodiment, second metallic layer 12-1 and third metallic layer 12-2 are each composed of titanium. A vertical thickness of each of second metallic layer 12-1 and third metallic layer 12-2 may, for example, be in the range of from 10 nm to 20 nm, such as in the range of from 13 nm to 17 nm.

In a specific embodiment, the thicknesses of first metallic layer 122 and fourth metallic layer 123 are 30 nm each, those of first dielectric layer 11, second dielectric layer 111 and third dielectric layer 112 are 65 nm each, and those of second metallic layer 12-1 and third metallic layer 12-2 are 15 nm each. First metallic layer 122 and fourth metallic layer 123 are composed of tantalum, first dielectric layer 11, second dielectric layer 111 and third dielectric layer 112 are composed of titanium dioxide, and second metallic layer 12-1 and third metallic layer 12-2 are each composed of titanium.

Figure 3A:
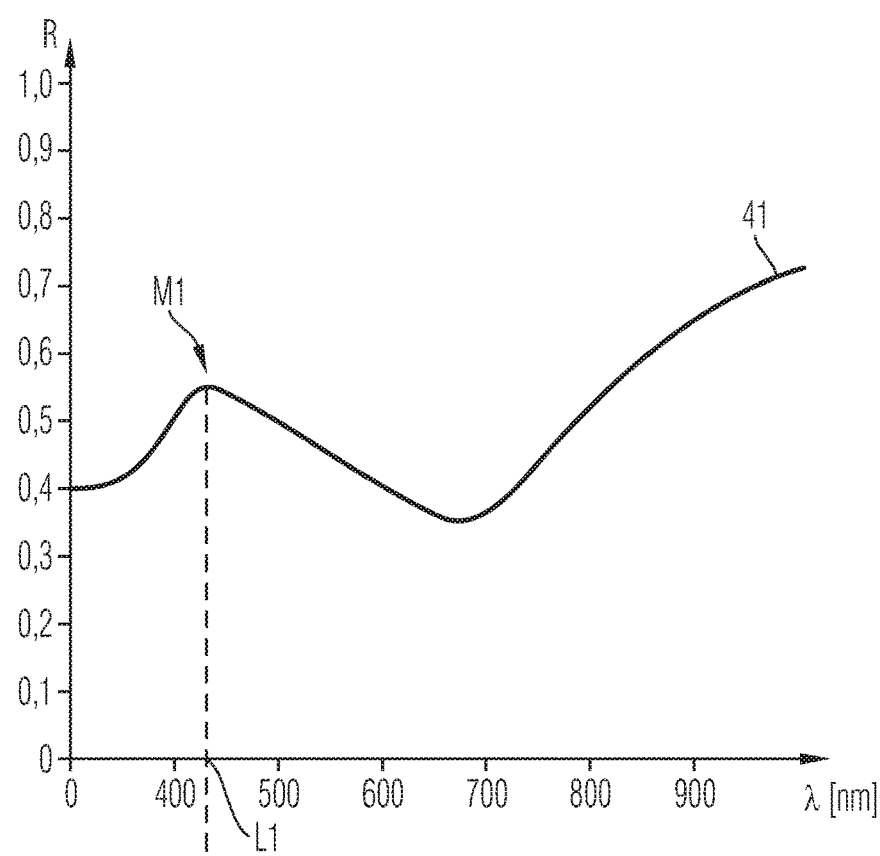
FIG. 3A is a plot illustrating the spectral reflectivity of the surface coating of FIG. 2A.

FIG. 3A shows a plot illustrating the first spectral reflectivity 41 of surface coating 1 of FIG. 2A for the aforedescribed exemplary embodiment, in which: first metallic layer 122 and fourth metallic layer 123 are composed of tantalum and have a thickness of 30 nm each; first dielectric layer 11, second dielectric layer 111 and third dielectric layer 112 are composed of titanium dioxide and have a thickness of 65 nm each; and second metallic layer 12-1 and third metallic layer 12-2 are composed of titanium and have a thickness of 15 nm each. Spectral reflectivity 41 is plotted as the ratio R of reflected power to incident power over the wavelength y in nm. Thus, curve 41 is characteristic of the interference filter of surface coating 1 in the first state and represents the first spectral reflectivity. First spectral reflectivity 41 has a first reflectivity maximum M1 at a first wavelength L1 slightly above 400 nm. First reflectivity maximum M1 is the maximum value of reflectivity 41 in the visible spectrum. Thus, this corresponds to a preferred reflection of light in the green-blue region of the spectrum. Overall, therefore, a blue color appearance is produced in the first state due to the first spectral reflectivity 41. The color appearance is substantially independent of the selected viewing angle (with respect to surface coating 1). This means that the color appearance is stable with respect to a change in viewing angle, at least in a range of between 0° and 60°, where 0° corresponds to a viewing direction perpendicular to surface coating 1.

When, during clinical reprocessing, surface coating 1 of FIG. 2A is subjected to an autoclaving process and/or a treatment with a base, for example a base having a pH>10, second metallic layer 12-1 and third metallic layer 12-2 are oxidized. In the process, the base may reach second metallic layer 12-1 and third metallic layer 12-2 are oxidized through pinholes which are automatically formed during the formation of the layers located thereabove. In a variant, it is also possible that defined accesses are patterned in the overlying layers for this purpose. Thus, in a specific embodiment, metallic layers 12-1, 12-2 are converted by oxidation to dielectric and transparent titanium dioxide layers 12'-1, 12'-2. This is shown in FIG. 2B, which illustrates the second state of surface coating 1 after the sterilization treatment.

Figure 3B:
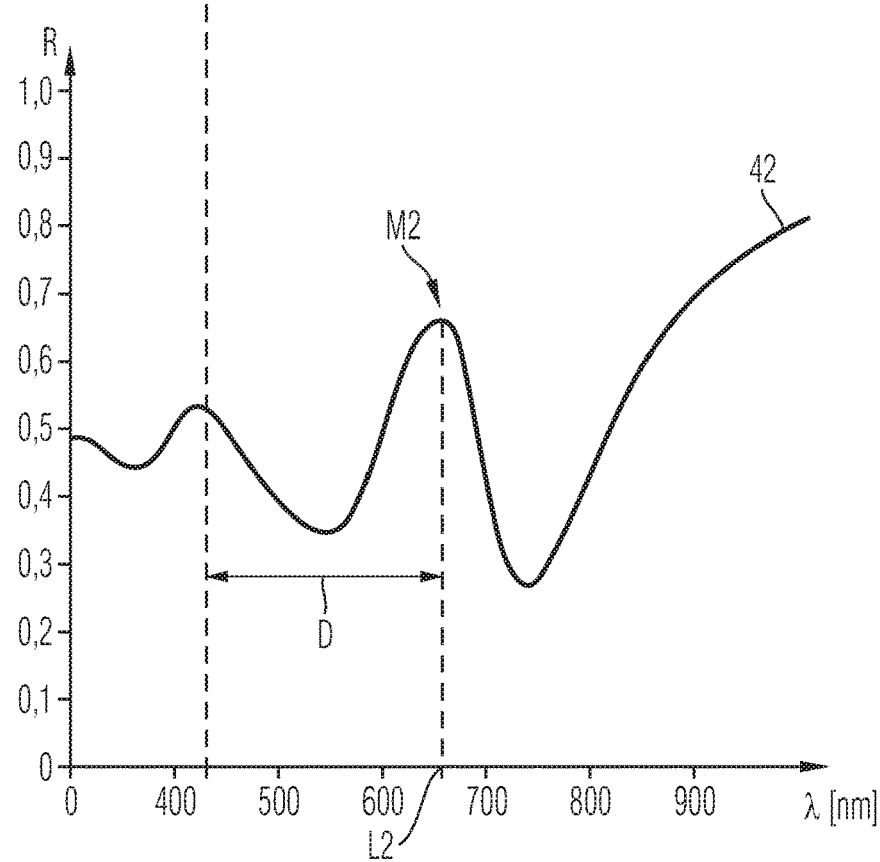
FIG. 3B is a plot illustrating the spectral reflectivity of the surface coating of FIG. 2B.

In the second state, due to the interference behavior of titanium dioxide layers 12'1, 12'-2, the interference filter of surface coating 1 has an altered, second spectral reflectivity 42, which is plotted in FIG. 3B. Second spectral reflectivity 42 has a clear second reflectivity maximum M2. Second reflectivity maximum M2 is at a second wavelength L2 in the red region, approximately at 650 nm. Thus, difference D between second wavelength L2 and first wavelength L1 is greater than 200 nm. Overall, therefore, an orange-red color appearance is produced in the second state (again substantially regardless of the viewing angle). Accordingly, the orange-red color of medical instrument 2 indicates that it has been subjected to a clinical reprocessing procedure.

Figure 4A:
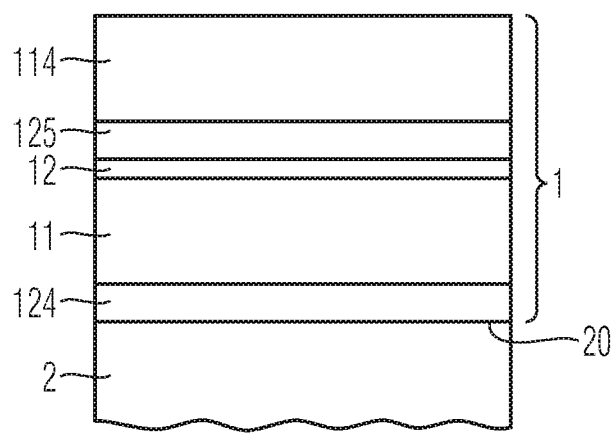
FIG. 4A is a vertical cross-sectional view showing a portion of a surface coating in a first state.
Figure 4B:
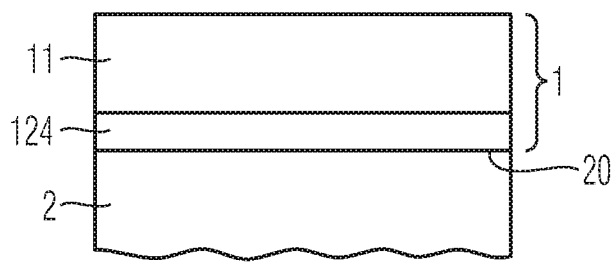
FIG. 4B shows the surface coating of FIG. 4A in a second state after a sterilization treatment.

FIGS. 4A and 4B show another specific embodiment, where, as described above with reference to FIGS. 2A and 2B, medical instrument 2 may be a surgical hand instrument or a part of it, such as a single-use drill. Surface 20 of medical instrument 2 may be formed of, for example, a substrate layer of stainless steel, such as the commonly used 316L steel. Alternatively, substrate layer 2 may be composed of, for example, cobalt-chromium alloy CoCr28Mo6.

In the first state shown in FIG. 4A, surface coating 1 includes a stack composed of the following layers: a first metallic layer 124 disposed on surface 20; a first dielectric layer 11; a second metallic layer 12, a third metallic layer 125; and a second dielectric layer 114. These layers are arranged one above another in the order in which they are mentioned above, starting at surface 20 of medical instrument 2, so that second dielectric layer 114 finishes stack 1 off at the top.

First metallic layer 124 and third metallic layer 125 may be composed of tantalum. First metallic layer 124 and third metallic layer 125 may, for example, each have a thickness in the range of from 10 nm to 90 nm, such as in the range of from 30 nm to 70 nm.

First dielectric layer 11 and second dielectric layer 114 may be composed of titanium dioxide. A vertical layer thickness of first dielectric layer 11 is, for example, in the range of from 270 nm to 310 nm, such as in the range of from 280 nm to 300 nm. A vertical thickness of second dielectric layer 114 may, for example, be in the range of from 140 nm to 150 nm, such as in the range of from 143 nm to 147 nm.

In a specific embodiment, second metallic layer 12 is composed of magnesium. A vertical thickness of second metallic layer 12 may, for example, be in the range of from 5 nm to 50 nm, such as in the range of from 10 nm to 30 nm.

In an exemplary embodiment, first metallic layer 124 and third metallic layer 125 are each composed of tantalum and have a thickness of 50 nm, and first dielectric layer 11 and second dielectric layer 114 are each composed of titanium dioxide, first dielectric layer 11 being 290 nm thick and second dielectric layer 114 being 145 nm thick. Second metallic layer 12 is composed of magnesium and is 10 nm thick.

FIG. 4B shows a second state, to which surface coating 1 is irreversibly converted during a sterilization treatment of medical instrument 2. During the sterilization treatment, surface coating 1 may, for example, be subjected to a treatment with a base, for example a base having a pH>10, and/or to an autoclaving process. In clinical practice, it is common, for example, to perform autoclaving; i.e., sterilization treatments with moist heat, at temperatures in the range of from 121° C. to 135° C. at an absolute pressure of from 1 to 5 bar for a period of from 1 to 30 minutes. When surface coating 1 is exposed to such conditions, second metallic layer 12 oxidizes and, as a result, delaminates from first dielectric layer 11. In a rinsing process during the sterilization treatment, the upper sub-stack composed of the (oxidized) second metallic layer 12, third metallic layer 125, and second dielectric layer 114 may then be irreversibly detached from first dielectric layer 11 and removed.

Due to the detachment of the upper sub-stack, the spectral reflectivity of surface coating 1 is changed, so that, similarly to the exemplary embodiment described above with reference to FIGS. 2A-3B, a color change from the green to the red region may occur, such color change being clearly perceptible to the human eye.

Figure 5A:
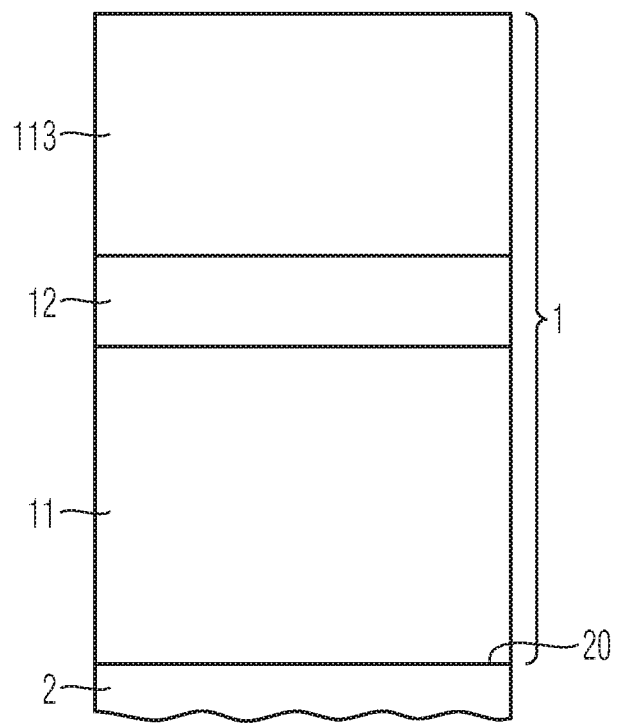
FIG. 5A is a vertical cross-sectional view showing a portion of a surface coating in a first state.

FIG. 5A shows in vertical cross section a portion of a surface coating 1 for a medical instrument 2 in accordance with a fourth exemplary embodiment. Medical instrument 2 may be a surgical hand instrument, such as a single-use scalpel. Surface coating 1 is disposed on a surface 20 of medical instrument 2. Surface 20 may be formed, for example, from a substrate layer of a commonly used stainless steel, such as 316L steel.

Surface coating 1 may be formed on surface 20 by reactive arc evaporation, for example. This may be done in a masked process, so that surface coating 1 may be deposited, for example, on the handle of the scalpel circularly around the circumference thereof.

In the first state depicted in FIG. 5A, surface coating 1 includes a stack composed of a first dielectric layer 11, a metallic layer 12, and a second dielectric layer 113. First dielectric layer 11 is disposed on surface 20 of the substrate layer of medical instrument 2. Metallic layer 12 is disposed on first dielectric layer 11. Second dielectric layer 113 is disposed on metallic layer 12 and finishes stack 1 off at the top.

In a specific embodiment, first dielectric layer 11 is composed of titanium dioxide. First dielectric layer 11 may, for example, have a thickness in the range of from 105 nm to 125 nm, such as in the range of from 110 nm to 120 nm, in the vertical direction.

In a specific embodiment, metallic layer 12 is composed of magnesium. A vertical layer thickness of metallic layer 12 may, for example, be in the range of from 5 nm to 50 nm, such as in the range of from 10 nm to 30 nm.

In a specific embodiment, second dielectric layer 113 is also composed of titanium dioxide. A vertical thickness of second dielectric layer 113 may, for example, be in the range of from 135 nm to 155 nm, such as in the range of from 140 nm to 150 nm In a specific embodiment, first dielectric layer 11 is composed of titanium dioxide and has a thickness of 115 nm, metallic layer 12 is composed of magnesium and has a thickness of 20 nm, and second dielectric layer 113 is composed of titanium dioxide and has a thickness of 145 nm.

In the first state shown in FIG. 5A, surface coating 1 has a first spectral reflectivity. If first dielectric layer 11 is, for example, a 115 nm thick titanium dioxide layer, metallic layer 12 is a 20 nm thick magnesium layer, and second dielectric layer 113 is a 145 nm thick titanium dioxide layer, then a green color appearance is produced when surface coating 1 is viewed under white light. This is because the light components that are reflected at the outer interface of second dielectric layer 113 interfere constructively and destructively with green light components which enter second dielectric layer 113 (experiencing a phase shift of 180°) and are reflected at the inner interface with metallic layer 12.

Figure 5B:
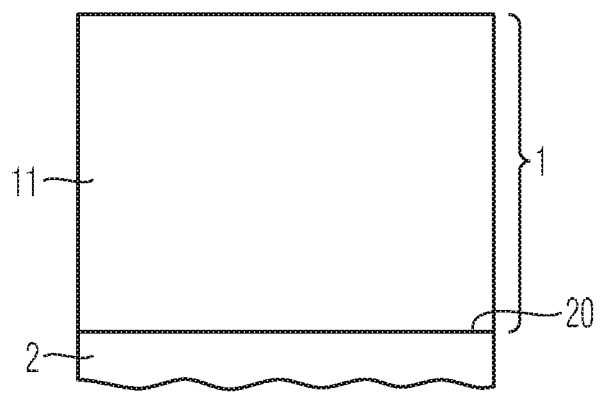
FIG. 5B shows the surface coating of FIG. 5A in a second state subsequent to a sterilization treatment.

If medical instrument 2 is clinically reprocessed by a sterilization treatment, then surface coating 1 is thereby irreversibly converted to the second state shown in FIG. 5B. During the sterilization treatment, surface coating 1 may, for example, be subjected to an autoclaving process. In clinical practice, it is common, for example, to perform autoclaving; i.e., sterilization treatments with moist heat, at temperatures in the range of from 121° C. to 135° C. at an absolute pressure of from 1 to 5 bar for a period of from 1 to 30 minutes. When surface coating 1 is exposed to such conditions, metallic layer 12 oxidizes and, as a result, delaminates from first dielectric layer 11. In a rinsing cycle during the sterilization treatment, the upper sub-stack composed of the (oxidized) metallic layer 12 and second dielectric layer 113 may then be irreversibly detached from first dielectric layer 11 and removed. As an ultimate result, in the second state, the surface coating 1 shown in FIG. 5B has a second spectral reflectivity which results in a red color appearance when illuminated with white light.

It should be noted that the various metal-dielectric stacks 1 shown in FIGS. 1A through 2B and 3A through 5B are not necessarily shown true-to-scale in terms of the individual layer thicknesses. In addition to the layer thicknesses specified above by way of example, other different thicknesses are also possible. The interference colors of individual transparent layers, which result from constructive and destructive interference at the interference filter, can be obtained in known manner by suitably selecting the layer thicknesses and, to this end, may also be simulated, for example.

The aforedescribed exemplary embodiments of surface coatings are also applicable to a microfluidic device, such as a so-called "flow cell," in this or a similar way. Such microfluidic devices are frequently used in the context of molecular medical techniques for diagnostic purposes, such as in DNA sequencing. During normal initial use and/or during a sterilization treatment of such a microfluidic device, the surface coating may be exposed to a corrosive environment and thereby converted from a first to a second state While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS 1 surface coating
11 dielectric layer
111, 112, 113, 114 further dielectric layers
12, 12-1, 12-2 metallic layer
12', 12'-1, 12'-2 (previously) metallic layer after a sterilization treatment
121, 122, 123, 124, 125 further metallic layers
2 medical instrument
20 surface
41 first spectral reflectivity
42 second spectral reflectivity
D difference
L1 first wavelength
L2 second wavelength
M1 first reflectivity maximum
M2 second reflectivity maximum

What is claimed is:

1. A surface coating for a medical instrument, the surface coating comprising:
    an interference filter having at least one dielectric layer and at least one metallic layer arranged one above another,
    wherein at least one of the at least one metallic layer and the at least one dielectric layer is adapted to be structurally altered by action of a corrosive environment on the surface coating such that the surface coating is convertible from a first state to a second state,
    wherein, in the first state, the surface coating has a first spectral reflectivity and, in the second state, the surface coating has a second spectral reflectivity that is different from the first spectral reflectivity, and
    wherein the first spectral reflectivity has a first reflectivity maximum at a first wavelength, and the second spectral reflectivity has a second reflectivity maximum at a second wavelength, a difference between the second wavelength and the first wavelength being at least 100 nm.

2. The surface coating as recited in claim 1, wherein, when illuminated with white light, the surface coating has a first color in the first state and a second color in the second state, the second color being different from the first color.

3. The surface coating as recited in claim 1, wherein the at least one metallic layer is adapted to be oxidized and/or to be detached from the at least one dielectric layer or another layer of the surface coating by the action of the corrosive environment, whereby the surface coating is convertible to the second state.

4. The surface coating as recited in claim 1, wherein the at least one metallic layer is composed of at least one of titanium and magnesium.

5. The surface coating as recited in claim 1, wherein the at least one dielectric layer is composed of titanium dioxide.

6. The surface coating (1) as recited in claim 1, wherein the surface coating is convertible to the second state by a sterilization treatment in which the surface coating is exposed to the corrosive environment.

7. The surface coating as recited in claim 6, wherein the sterilization treatment is at least one of an autoclaving process and a treatment of the surface coating with a base.

8. The surface coating as recited in claim 1, wherein the at least one metallic layer is adapted to increase optical transparency or to change from an optically non-transparent state to an optically transparent state under the action of the corrosive environment.

9. The surface coating as recited in claim 1, wherein the interference filter includes at least one of a plurality of dielectric layers and a plurality of metallic layers.

10. A medical instrument having a surface coating according to claim 1.

11. The medical instrument as recited in claim 10, wherein the medical instrument is at least one of a hand instrument, a device for implantation into a human or animal body and a microfluidic device.

12. A method for producing a surface coating for a medical instrument, the method comprising:
   providing a medical instrument having a surface; and
   producing on the surface an interference filter including at least one dielectric layer and at least one metallic layer arranged one above another,
   wherein at least one of the at least one metallic layer and the at least one dielectric layer is adapted to be structurally altered by action of a corrosive environment on the surface coating such that the surface coating is convertible from a first state to a second state,
   wherein, in the first state, the surface coating has a first spectral reflectivity and, in the second state, the surface coating has a second spectral reflectivity that is different from the first spectral reflectivity, and
   wherein the first spectral reflectivity has a first reflectivity maximum at a first wavelength, and the second spectral reflectivity has a second reflectivity maximum at a second wavelength, a difference between the second wavelength and the first wavelength being at least 100 nm.

13. A surface coating for a medical instrument, the surface coating comprising:
   an interference filter having at least one dielectric layer and at least one metallic layer arranged one above another,
   wherein at least one of the at least one metallic layer and the at least one dielectric layer is adapted to be structurally altered by action of a corrosive environment on the surface coating such that the surface coating is convertible from a first state to a second state,
   wherein, in the first state, the surface coating has a first spectral reflectivity and, in the second state, the surface coating has a second spectral reflectivity that is different from the first spectral reflectivity, and
   wherein the interference filter includes at least one of a plurality of dielectric layers and a plurality of metallic layers.

* * * * *